(12) United States Patent
Shooshtari et al.

(10) Patent No.: US 8,378,094 B2
(45) Date of Patent: Feb. 19, 2013

(54) POLYMERIZATION INITIATORS FOR FIBER-REINFORCED POLYMER COMPOSITES AND MATERIALS MADE FROM THE COMPOSITES

(75) Inventors: Kiarash Alavi Shooshtari, Littleton, CO (US); Jawed Asrar, Englewood, CO (US); Rajappa Tadepalli, Littleton, CO (US); Thomas Burghardt, Parker, CO (US); Klaus Friedrich Gleich, Highlands Ranch, CO (US)

(73) Assignee: Johns Manville, Denver, CO (US)

( * ) Notice: Subject to any disclaimer, the term of this patent is extended or adjusted under 35 U.S.C. 154(b) by 326 days.

(21) Appl. No.: 12/724,024

(22) Filed: Mar. 15, 2010
(Under 37 CFR 1.47)

(65) Prior Publication Data

US 2010/0280239 A1   Nov. 4, 2010

Related U.S. Application Data

(63) Continuation-in-part of application No. 12/008,041, filed on Jan. 8, 2008, now abandoned.

(51) Int. Cl.
*C07F 7/18* (2006.01)
(52) U.S. Cl. .................. 540/487; 548/406; 556/418
(58) Field of Classification Search .................. 540/487; 548/406; 556/418
See application file for complete search history.

(56) References Cited

U.S. PATENT DOCUMENTS

| | | | |
|---|---|---|---|
| 3,033,815 A * | 5/1962 | Pike et al. .................... | 528/38 |
| 3,621,001 A | 11/1971 | Steinhofer et al. | |
| 4,105,644 A | 8/1978 | Bukac et al. | |
| 4,188,478 A | 2/1980 | Goebel, Jr. | |
| 4,697,009 A | 9/1987 | Deschler et al. | |
| 5,782,908 A | 7/1998 | Cahalan et al. | |
| 5,864,007 A | 1/1999 | Schmid et al. | |
| 6,013,855 A | 1/2000 | McPherson et al. | |
| 6,358,557 B1 | 3/2002 | Wang et al. | |
| 6,579,965 B2 | 6/2003 | Hoogen et al. | |
| 2003/0096904 A1 | 5/2003 | Hakula et al. | |
| 2007/0072199 A1 | 3/2007 | Levicky et al. | |
| 2007/0123644 A1 | 5/2007 | Pfeiffer et al. | |
| 2010/0280239 A1 | 11/2010 | Shooshtari | |
| 2010/0286343 A1 | 11/2010 | Burghardt et al. | |
| 2011/0021737 A1 | 1/2011 | Tadepalli et al. | |
| 2011/0045275 A1 | 2/2011 | Tadepalli et al. | |

FOREIGN PATENT DOCUMENTS

| | | |
|---|---|---|
| EP | 2 289 690 A2 | 3/2011 |
| JP | 08 291186 | 11/1996 |
| WO | WO03084583 | 10/2003 |
| WO | 2004/046156 A1 | 6/2004 |
| WO | 2004/087719 A1 | 10/2004 |
| WO | 2005/094757 A1 | 10/2005 |

OTHER PUBLICATIONS

U.S. Appl. No. 12/008,041, Patent Office Communication Mailed Oct. 22, 2010.

* cited by examiner

*Primary Examiner* — Gregory Listvoyb
(74) *Attorney, Agent, or Firm* — Robert D. Touslee

(57) ABSTRACT

Coupling-initiator compounds are described that include a silicon-containing coupling moiety and at least one polymerization initiator moiety. The coupling moiety may be linked to the at least one polymerization initiator moiety by at least one linking moiety. The coupling moiety is capable of coupling the compound to a substrate, while the one or more polymerization initiator moieties are capable of initiating a polymerization of a monomer under polymerization conditions. The coupling-initiator compounds may be included in fiber reinforced polymer composites, where the compounds are coupled to the fibers in the composites and participate in the polymerization of the surrounding polymer.

9 Claims, No Drawings

POLYMERIZATION INITIATORS FOR FIBER-REINFORCED POLYMER COMPOSITES AND MATERIALS MADE FROM THE COMPOSITES

CROSS-REFERENCES TO RELATED APPLICATIONS

This application is a continuation-in-part of prior U.S. patent application Ser. No. 12/008,041, filed Jan. 8, 2008, the entire contents of which are hereby incorporated by this reference for all purposes.

BACKGROUND OF THE INVENTION

Inorganic materials may be used in composite articles to strengthen and reinforce the articles. In addition to increased dimensional stability, addition of the inorganic material provides polymer composites with significantly improved physical and mechanical properties. As one example, glass fibers may be placed into a polymer matrix where the high tensile strength of glass causes the matrix to become more rigid. The glass fibers incorporated in the polymer matrix may take various forms, such as continuous or chopped strands, rovings, woven or non-woven fabrics, and continuous or chopped strand mats.

Conventionally, glass fibers are formed by attenuating streams of a molten glass material from a bushing or orifice. The glass fibers may be attenuated by pulling by a winder, which collects filaments into a package or by other equipment or method capable of pulling the fibers. A sizing composition, or chemical treatment, is typically applied to the fibers after they are drawn from the bushing. After the fibers are treated with the sizing, which is typically in aqueous form, they may be dried in a package, chopped, or kept in the wet state before downstream processing.

Fiberglass may be mixed with a polymeric resin in an extruder and supplied to a compression- or injection-moulding machine to be formed into glass fiber-reinforced plastic composites. Typically, polymer pellets and fiberglass are fed together or separately into an extruder. During the extrusion process using single or twin-screw machines, the resin is melted and the fibers are dispersed throughout the molten resin to form a fiber/resin mixture. Next, the fiber/resin mixture may be degassed, cooled, and formed into pellets. The dry fiber strand/resin dispersion pellets are then fed to a moulding machine and formed into moulded composite articles that have a substantially homogeneous dispersion of glass fiber strands throughout the composite article.

Alternatively, in the process using continuous filaments, fiberglass filaments are mixed with the molten resin in an extruder with the screw geometry designed to mix the matrix with fibers without causing significant damage to the fibers. Obtained extruded materials are then subjected to compression moulding to form long-fiber reinforced thermoplastic materials with significantly improved mechanical properties due to the mostly unidirectional distribution of fiber.

Various chemical treatments exist for inorganic surfaces such as glass fibers to aid in their processability and applications. After fiber formation and before bundling, the filaments or fibers may be treated with a coating composition (sometimes referred to as a "sizing composition") that is applied to at least a portion of the surface of the individual filaments to protect them from abrasion, improve the chemical or physical bonding, and to assist in processing.

As used herein, the term "sizing composition", refers to any such coating composition applied to the filaments after forming. Sizing compositions may provide protection for subsequent processing steps, such as those where the fibers pass by contact points as in the winding of the fibers and strands onto a forming package, drying the sized fibers to remove the water and/or other solvent or melting of the film former on the fiber surface, twisting from one package to a bobbin, beaming to place the yarn onto very large packages ordinarily used as the warp in a fabric, chopping in a wet or dry condition, roving into larger bundles or groups of strands, unwinding, and other downstream processes. In addition, sizing compositions can play a dual role when placed on fibers that reinforce polymeric matrices in the production of fiber-reinforced plastics. In such applications, the sizing composition can provide protection as well as compatibility and/or chemical bonding between the fiber and the matrix polymer. Conventional sizing compositions typically contain one or more film forming polymeric or resinous components, glass-resin coupling agents, and one or more lubricants dissolved or dispersed in a liquid medium. The film forming component of the sizing composition is desirably selected to be compatible with the matrix resin or resins in which the glass fibers are to be embedded.

Many types of polymers may be reinforced by inorganic materials. Of particular note are those polymers formed by ring-opening polymerization reactions. Polyamides, such as poly(caprolactam), commonly know as "Nylon-6" or "polyamide-6", are examples of resins formed by ring-opening polymerization that are frequently reinforced by glass fibers. There is a need to provide glass-reinforced polyamide composites with high glass loading; however, one of the barriers is the high polymer viscosity of the polyamide in the molten state. This high viscosity hinders the dispersion of the glass fibers throughout the molten resin when the fiber/resin mixture is formed.

Anionic-catalysed ring-opening polymerization of lactams has become a commercially significant method for preparation of PA resins since these polymerizations can be conducted at relatively low temperatures and under atmospheric pressures. Caprolactam is by far the most studied lactam for such reactions and Nylon-6 prepared by this route compares favorably in properties with that prepared by conventional hydrolytic polymerization. Fast reaction kinetics, absence of by-products, and the crystalline nature of the Nylon so produced also makes anionic polymerization of lactams a compelling choice for several industrial applications, including reactive extrusion, reactive thermoplastic pultrusion, and reaction injection molding.

There is a need for new compounds and methods that allow increased loading and dispersion of a reinforcing material in a polymer composite. For example, there is a need for compounds and methods to increase the loading and dispersion of fiberglass in polymer matrices of thermoplastic and thermoset polymers These and other needs are addressed in the present application.

BRIEF SUMMARY OF THE INVENTION

Coupling-initiator compounds are described that contain moieties for both: (1) binding the compound to a substrate, and (2) initiating a polymerization reaction in the monomers surrounding the compound. The one or more initiator moieties on the compound may be capable of participating in an in situ ring-opening polymerization of a monomer in the presence of a polymerization catalyst when exposed to ring-opening polymerization conditions. As a result, substrates coupled to the compounds (e.g., organic or inorganic fibers) may be used as a ring-opening polymerization initiators, alone or with conventional polymerization initiators, in the formation of polymers that are reinforced with the inorganic material. As examples of substrates, mention may be made of glass, basalt, carbon fibers, carbon nanotubes, inorganic nanotubes, and metal fibers. For example, fiberglass substrates may be used in the formation of glass-reinforced polyamides.

The formation methods may include the use of the coupling-initiator compounds in compositions that treat the fiberglass before its mixture with the monomers that form the polymer component of the fiber reinforced composite. For example, a sized fiberglass substrate may be mixed with a lactam monomer and a polymerization catalyst to form a polymerization mixture, and the mixture may be exposed to conditions sufficient to cause an in situ anionic ring-opening polymerization of the lactam monomer, thereby forming a polymer/glass matrix in which the glass substrate is grafted to the polyamide polymer. The polymerization is referred to as "in situ" because the polymer is formed directly on the surface of the glass substrate, as opposed to being first formed and then coated on the glass surface. As a result, the coupling of the glass component and the polymer component of the composite material is substantially improved over conventional glass-reinforced resins.

Embodiments of the invention include a coupling-initiator compound having the formula:

S—X—(I)$_n$, wherein n is an integer having a value between 1 and 5; S may include a silicon-containing coupling moiety through which the coupling-initiator compound bonds to a substrate surface; X may include a linking moiety to link the S moiety with the one or more I moieties; and (I)$_n$ may include one or more polymerization initiator moieties. Each of the initiator moieties is capable of initiating a polymerization of a monomer under polymerization conditions, and each of the initiator moieties may be the same or different.

Embodiments of the invention may further include a coupling-initiator compound that includes the formula:

S—X—Y—I, wherein S may include a silicon-containing coupling moiety through which the coupling-initiator compound bonds to a substrate surface; X and Y may include linking moieties to link the S moiety with the I moiety; and I may include a polymerization initiator moiety. The initiator moiety is capable of initiating a polymerization of a monomer under polymerization conditions.

Embodiments of the invention may also include a coupling-initiator compound that includes the formula:

wherein S may include a silicon-containing coupling moiety through which the coupling-initiator compound bonds to a substrate surface; X may include a linking moiety to link the S moiety with the I$^1$ and I$^2$ moieties; and I$^1$ and I$^2$ may include polymerization initiator moieties. The initiator moieties are capable of initiating a polymerization of a monomer under polymerization conditions.

Embodiments of the initiator moieties may include blocked precursors, such as isocyanates blocked with compounds other than the precursors used to form the initiator moiety on the coupling-initiator compound. When the coupling-initiator compounds are exposed to polymerization conditions, the blocked isocyanate becomes unblocked to furnish free isocyanate. The isocyanate may, under the reaction conditions, contacts nearby monomer and forms the first part of polymerisation initiation group. The polymerization is initiated close to the substrate surface due to the attachments of the coupling-initiator compound to the surface through the coupling moiety.

Embodiments of the invention may still further include substrates coated with a sizing composition containing the present coupling-initiator compounds. Exemplary sizing compositions may include unblocked silane-functionalized isocyanate that reacts with caprolactam to produce 2-oxo-N-(3-(triethoxysilyl)propyl)azepane-1-carboxamide. The sizing composition is coupled to a glass fiber substrate, and the coated fibers can participate in the anionic ring-opening polymerization of caprolactam monomer.

Embodiments may yet further include methods of making reinforced resin material (e.g., a glass-reinforced resin polyamide) using the present coupling-initiator compounds. The methods may include applying a sizing composition with one or more coupling-initiator compounds to a glass substrate to make a sized glass substrate. The sized glass substrate may be mixed with a lactam monomer (e.g., caprolactam) and a polymerization catalyst to form a polymerization mixture that may then be exposed to conditions sufficient to cause an in situ anionic ring-opening polymerization of the lactam monomer. In additional embodiments, the sized glass substrate may be mixed with a cyclic olefin monomer (e.g., norbornene) and a polymerization catalyst to form a polymerization mixture that may then be exposed to conditions sufficient to cause an in situ ring-opening metathesis polymerization of the cyclic olefin monomer. The resulting composite products may include a matrix in which the glass substrate is grafted onto the polymer, substantially improving the coupling between the glass and the polymer.

Embodiments may yet further include methods of making reinforced resin materials into solid masses of a prescribed shape. The solid masses may be made by, for example, reactive extrusion, resin transfer molding, pultrusion, or reaction injection molding, among other types of forming processes.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

Compounds are described that are capable of both coupling to a substrate and initiating the polymerization of surrounding polymeric materials. The compounds may be referred to as "coupling-initiator" compounds to describe their dual functionality. Embodiments of the coupling-initiator compounds may be represented by general Formula I:

   (I)

wherein "S" represents a silicon-containing coupling moiety capable of bonding to the surface of an inorganic substrate, "I" represents a ring-opening polymerization initiator moiety or a blocked precursor thereof, and "X" and "Y" represent a linking moieties that link the S and "I" moieties. As examples of suitable X and Y moieties, mention may be made of alkyl, aryl, and alkyl-aryl groups.

Some specific classes of coupling-initiator compounds may include:

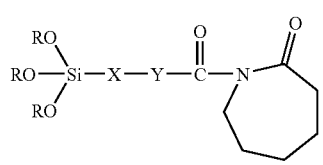   (1)

wherein X and Y may be, independently, an element or functional group such as carbon (—C—), nitrogen (—N—), oxygen (—O—), sulphur (—S—), silicon (—Si—), an amine group, an amide group, a urethane group, a urea group, an ether group, or an ester group, among other groups; X and Y may also be, $R^1$—X' and Y'—$R^2$, wherein X' and Y' may be a covalent bond or an element or functional group as described above, and $R^1$ and $R^2$ may be, independently:

a $(CH_2)_n$ group, where $0 \leq n \leq 36$;
a branched aliphatic group;
a cycloaliphatic group;
an aromatic group; or
a combination of these groups.

$R^3$, $R^4$, and $R^5$ may be the same or different, and each represent a hydrogen, an alkyl (e.g., a $C_1$-$C_4$ alkyl group), an aryl, an alkoxy, a halo, or an alkyl-cyclic group.

Some specific examples of coupling-initiator compounds may include:

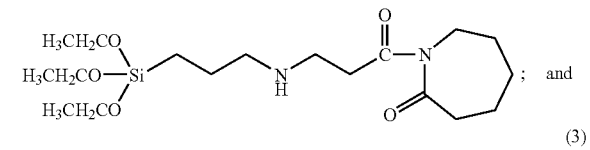   (2)

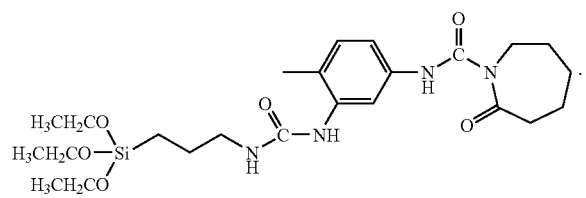   (3)

The coupling-initiator compounds shown above have increased thermal stability due to the separation or stabilization of the HN—CO bond. In the case of compound (2) above, the NH—CO bond is separated by an ethylene (—$CH_2$—$CH_2$—) chain. The separation of the bond increases the thermal stability of the compound compared with a similar compound that is missing the ethylene separation group. In the case of compound (3) above, the aromatic ring coupled to the nitrogen side of the HN—CO bond helps stabilize the bond, which also increases its thermal stability.

The increased thermal stability may make coupling-initiator compounds such as (2) and (3) more adaptable for making composite materials. For example, the coupling-initiator compounds may be subjected to raised temperatures when coated onto substrates such as fibers. When the coated fibers are dried, the compounds may be subjected to temperatures high enough to destabilize the HN—CO bond or some other linkage on the compound that reduces or eliminates the compound's ability to initiate polymerization reactions. Thus, adjusting the thermal stability of the compounds to remain stable during pre-polymerization substrate treatment steps may be advantageous.

Embodiments of the coupling-initiator compounds may also be represented by general Formula (II):

   (II)

wherein, similar to Formula (I) above, "S" represents a silicon-containing coupling moiety through which the compound may be bonded to a substrate (e.g., a glass substrate), "I" represents a ring-opening polymerization initiator moiety, or a blocked precursor thereof, and "X" represents a linking moiety capable of linking the S moiety and the I moiety.

Embodiments of the coupling-initiator compounds may also include a plurality of initiator moieties "I". These coupling-initiator compounds may include classes of compounds with general formulas S—X—Y—$(I)_n$, and S—X—$(I)_n$, where $1 \leq n \leq 6$. For example, coupling-initiator compounds with dual-initiator cites may be represented by general Formula (III):

   (III)

wherein S represents a silicon-containing coupling moiety capable of bonding to the surface of an inorganic substrate, $I^1$ and $I^2$ represent the same or different polymerization initiator moieties or blocked precursors thereof, and "X" represents a linking moiety that links the S and $I^1$ and $I^2$ moieties. The initiator moieties may be ring-opening polymerization initiator moieties.

In Formulas (I), (II) and (III) above, the silane coupling moiety S may comprise any of the known functional groups that react with the surface of an inorganic substrate, e.g., a silanol or organosilane group. Compounds containing organosilane groups are well known coupling agents in material systems that consist of an inorganic (e.g., glass) and organic (e.g., polymer) phase, and serve to covalently bond the organic groups in the compound to groups on the inorganic surface. As one example, S may comprise an organosilane group of the following Formula (IV):

   (IV)

wherein X may be the same as defined in Formulas (I), (II), and (III) above; and $R^3$, $R^4$ and $R^5$ may be the same or different, and each represent alkyl, aryl, alkoxy, halo, or a alkylcyclic group. In some instances, X may be directly connected to one or more of $R^3$, $R^4$ and/or $R^5$.

Alternative embodiments may include coupling moieties that substitute a different element for the silicon in the moiety. For example, a transition metal such as titanium (i.e., a titanate) or zirconium (i.e., a zirconate) may replace the silicon in the coupling moiety.

The ring-opening polymerization initiator moiety "I" may be any known organic reactive group that participates in a ring-opening polymerization reaction, which term includes anionic ring-opening polymerization, cationic ring-opening polymerization and ring-opening metathesis polymerization (ROMP). For example, such reactive group may participate in the polymerization by forming a reactive center where further cyclic monomers can join after opening to provide a larger polymer chain through ionic propagation.

In one embodiment, the "I" moiety may be a group that serves the function of an initiator in the anionic ring-opening polymerization of a lactam or a lactone, e.g., "I" may be an N-substituted imide group. These polymerization reactions are described in U.S. Pat. Nos. 3,621,001; 4,188,478; 5,864,007; 6,579,965; all of which are incorporated by reference for all purposes. Generally, these polymerizations are conducted at low temperatures (80-160° C.), below the melting point of the resulting polyamides (which is typically above 200° C.), and typically employ, in addition to the initiator compound, two other components; such as a lactam monomer and a polymerization catalyst. The monomer component may be a lactam or lactone having from 3 to 12 carbon atoms in the main ring, such as caprolactam and caprolactone. The polymerization catalyst may be an alkali metal salt of the lactam or lactone monomer, such as sodium caprolactam. There may also be other known auxiliary components in the polymerization mixture (e.g., co-initiators, catalysts, co-catalysts, electron donors, accelerators, sensitizers, processing aids, release agents, etc.).

Polymerizations with Coupler-Initiator Compounds

In the anionic ring-opening polymerization of the lactam or lactone monomer, the combination of monomer and polymerization catalyst produces a catalyzed monomer species containing an atom with a reactive free anion. As used herein, the term "ring-opening polymerization initiator" may be used to denote this catalyzed monomer species, and the term "ring-opening polymerization initiator moiety" may be defined as a group that reacts with the catalyzed monomer molecule to cleave the lactam ring and start the initial growth of the polymeric chain. In one embodiment the polymerization catalyst may comprise an alkali metal salt of the lactam or lactone and the initiator moiety may comprise an N-substituted imide group, e.g. an N-acyl lactam group.

As another example, in the ring-opening metathesis polymerization (ROMP) of a cyclic olefin monomer such a norbornene, cyclopentadiene, cyclooctadiene, decyclopentadiene, etc., the "I" moiety of the compound of Formula I above may be a cyclic olefin-substituted imide group that undergoes ROMP under catalytic conditions using a heavy metal alkylidene catalyst such as developed by R. R. Schrock or R. Grubbs. In this case the "I" moiety becomes part of the polymer chain.

As specific examples of coupling-initiator compounds of Formula I above that are useful in the anionic ring-opening polymerization of lactams, mention may be made of certain N-propylsilyl-N'-acyl-ureas described in U.S. Pat. No. 4,697,009, incorporated by reference herein. In one embodiment, the coupling-initiator compound may comprise 2-oxo-N-(3-(triethoxysilyl)propyl)azepane-1-carboxamide.

Methods of Making the Coupling-Initiator Compounds

1. Exemplary Formula (I) Coupling-Initiator Compounds

Exemplary coupling-initiator compounds having Formula (I) above may be prepared by reacting an aminoalkyltrialkoxy silane 1 with a methyl acrylate compound 2 to form an intermediate 3 with a reactive ester moiety. A caprolactam 4 (e.g., sodium caprolactam) may be introduced to the intermediate 3 to form the coupling-initiator product 5. An exemplary reaction scheme A showing selected steps in the synthesis may be shown as:

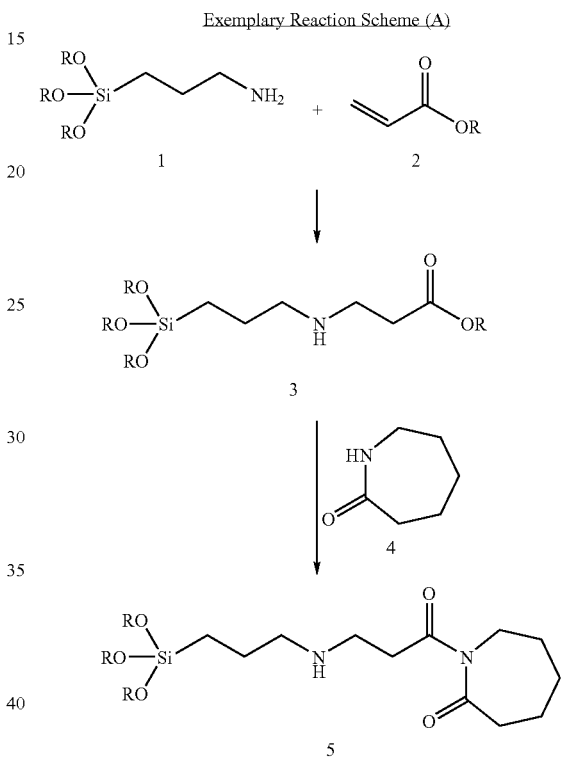

In a specific example of making a coupling-initiator compound (5), 221.4 g (1 mole) of 3-aminopropyltriethoxy silane (1) and 86.1 g (1 mole) of methyl acrylate (2) are mixed in a 1000 ml flask equipped with a condenser and a magnetic stirrer bar at ambient temperature. The temperature of the mixture is then maintained at 40-50° C. for one hour. Then, 128.4 g (0.95 moles) of sodium caprolactam (4) is added to the clear liquid product in the flask, and the temperature of the mixture raised to about 80° C. for about two hours to produce the coupling-initiator product (5).

Embodiments may include interrupting exemplary reaction scheme A with the formation of intermediate (3) containing the ester precursor to the initiator moiety. The intermediate (3) may be used instead of final coupling-initiator product (5) in coatings and sizing compositions for a substrate used as a solid reinforcing component of a polymer composite material. For example, the silicon-containing moiety on intermediate (3) may be reacted with a glass fiber substrate to bond the intermediate (3) to the surface of the fibers. The intermediate (3) coated fibers may then be incorporated into a monomer mixture that includes caprolactam (4), which under reaction conditions will react with ester end of the intermediate to produce the initiator moiety of the coupling-initiator compound.

The reaction conditions may be set such that the caprolactam (4) reacts with the ester moiety, but the initiator moiety that is produced does not initiate a ring-opening polymerization reaction with the surrounding monomer. Alternatively, the reaction conditions may be set such that both the initiator moiety is formed and the ring-opening polymerization reaction is initiated. For example, the temperature of the mixture of the coated glass fibers and monomer solution may be set lower (e.g., about 40° C. to about 50° C.) to produce the initiator moiety without initiating the polymerization reaction and set higher (e.g., about 80° C. to about 200° C.), or increased from the lower temperature, to initiate the polymerization reaction.

An alternate synthesis route to the one shown in reaction scheme A above may first react the caprolactam (4) with the methyl acrylate (2) for about one hour. Then the 3-aminopropyltriethoxy silane (1) may be added to the viscous reaction product and stirred for about three hours at 40-50° C. to produce the coupling-initiator product (5). Alternately, an acryloyl chloride compound (2b) may be used instead of the methyl acrylate (2) to produce caprolactam intermediate (3b) reacts with the silane compound (1) to produce the coupling-initiator product (5), as shown in reaction scheme B below:

Exemplary Reaction Scheme (B)

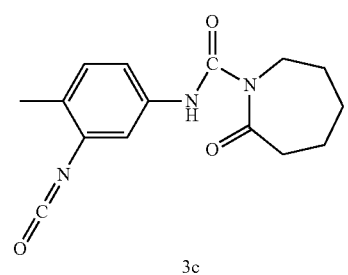

Additional embodiments for methods of making coupling-initiator compounds having Formula (I) may include substituting an isocyanate-containing reactant for an acrylate reactant. For example, an aromatic diisocyanate compound such as 2,4 toluene diisocyanate (2c) may be reacted with a caprolactam (4c) to produce a intermediate (3c), that reacts with a silicon-containing reactant such as 3-aminopropyltrialkoxy silane (1c) to produce the final coupling-initiator product (5c) as shown in exemplary reaction scheme (C) below:

Exemplary Reaction Scheme (C)

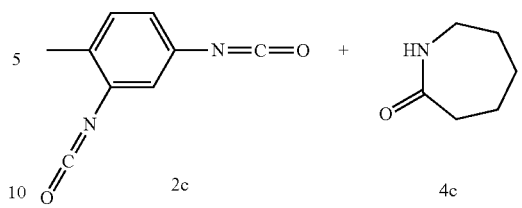

In a specific example of making a coupling-initiator compound 5c, 174.2 g (1 mole) of 2,4 toluene diisocyanate is in solution with 1000 mL of 1,4 dioxane in a 2000 mL flask equipped with a condensate and magnetic stir bar. 113.2 g (1 mole) of caprolactam is added to the solution, and the temperature is raised to 100° C. and kept there for 4 hours. The solution is then cooled to ambient temperature in a water bath and 221.4 g (1 mole) of 3-aminopropyltriethoxy silane is added slowly as the solution temperature is kept below 50° C. After 30 minutes, the solid coupling-initiator product is isolated by evaporating the dioxane.

While the specific example above uses 2,4 toluene diisocyanate, other isocyanates may be used in lieu of (or in addition to) this reactant. For example, isocyanates having alophanate, biurete, and/or uretadione functional groups, among other functional groups, may be used. Also, contemplated are variations in the times, temperatures, and solvents used in the specific example. For example, pyridine may be used instead of dioxane as a solvent.

2a. Exemplary Formula (II) Coupling-Initiator Compounds

Coupling-initiator compounds having Formula (II) above may be prepared in accordance with the process set forth in the aforementioned incorporated U.S. Pat. No. 4,697,009. For example, the coupling-initiator compounds may be prepared by mixing in an aprotic, polar organic solvent such as N,N-dimethylformamide equimolar amounts of an alkali isocyanate (e.g. sodium isocyanate or potassium isocyanate), a 3-halopropyl silane (e.g. 3-chloropropyltriethoxysilane) and caprolactam, and reacting the ingredients with each other at elevated temperature. At the end of the reaction and cooling the mixture to room temperature, the precipitated alkali halide may be filtered off and the solvent may be removed from the filtrate to obtain the desired blocked isocyanate compound. Alternatively, coupling-initiator compounds may be prepared according to the procedure describe in International Patent No. WO 2006/012957, incorporated herein by reference.

In another embodiment, the coupling-initiator, 2-oxo-N-(3-(triethoxysilyl)propyl)azepane-1-carboxamide may be prepared in accordance with the following reaction scheme A':

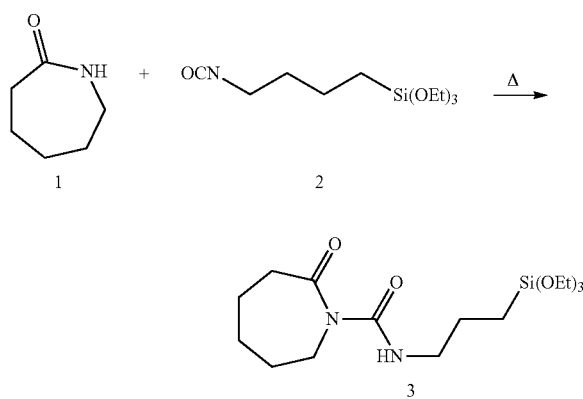

1.1 eq. of caprolactam 1 may be mixed with 1.0 eq. of 3-isocyanatopropyltriethoxysilane 2 and the mixture heated at 80-100° C. until the completion of the reaction and formation of 2-oxo-N-(3-(triethoxysilyl)propyl)azepane-1-carboxamide 3. The reaction progress can be measured by FT-IR, where disappearance of the isocyanate peak at 2300 cm$^{-1}$ should be observed. The reaction may be run neat or in solution, with 1,4-dioxane as the solvent. Organotin catalyst (e.g., dibutyltin dilaurate) may be used to significantly improve the reaction rate.

In one embodiment, a coupling activator compound of the invention may be used as the sole initiator in a anionic ring-opening polymerization reaction, or may be used in combination with other known initiator compounds. For example, compound 3 above may be used as the initiator in the reactive extrusion of Nylon-6 in accordance with the following reaction scheme B':

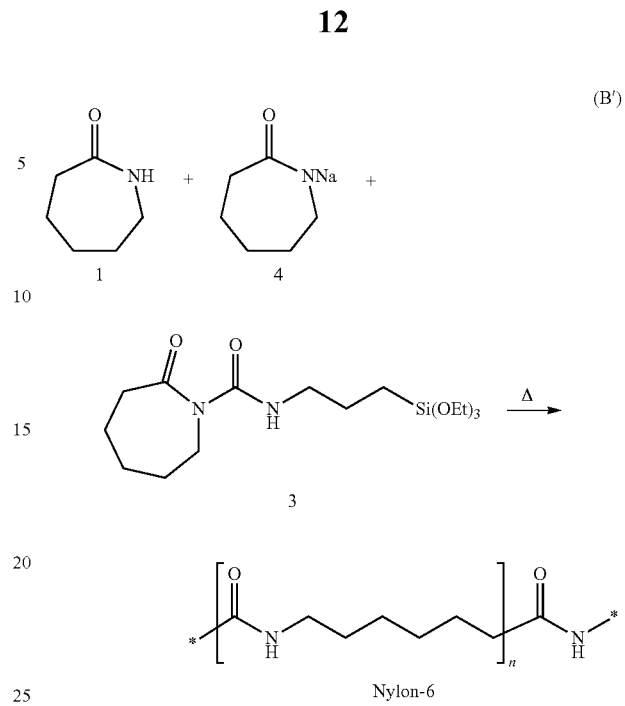

In the above reaction, 97.5 wt % of caprolactam 1 may be mixed with 1.5 wt % of the polymerization catalyst sodium caprolactam 4, and 1.0 wt % of 2-oxo-N-(3-(triethoxysilyl)propyl)azepane-1-carboxamide 3. The mixture may be fed into a twin-screw extruder with temperature profile of 80-205° C. at the screw speed of 78 min$^{-1}$ at torque of 4.8-9.6 MPa to accomplish ring-opening polymerization and obtain Nylon-6. Alternatively, the same results may be achieved by running the reaction in a beaker instead of using the reactive extrusion process.

In another embodiment, a coupling-initiator compound may participate in a ROMP reaction such as shown in the following reaction scheme C':

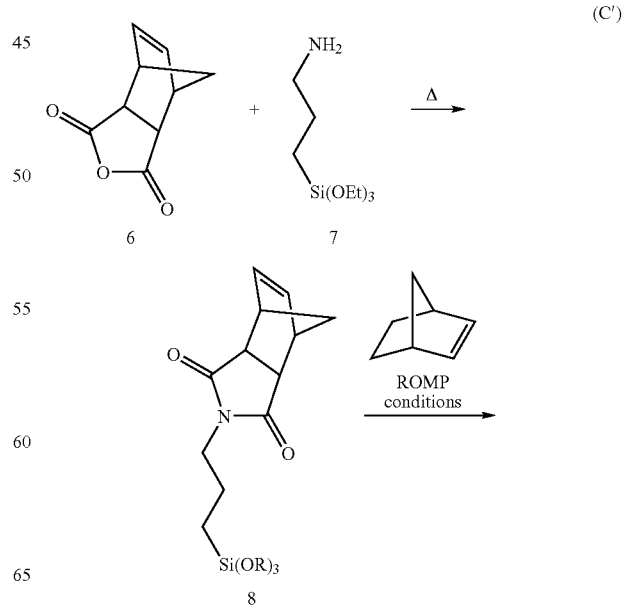

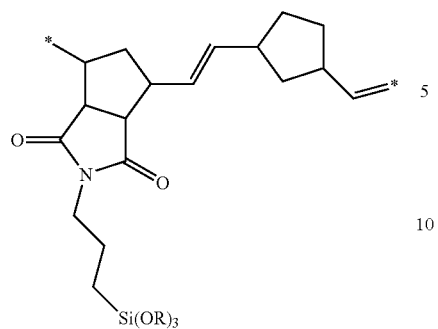

9

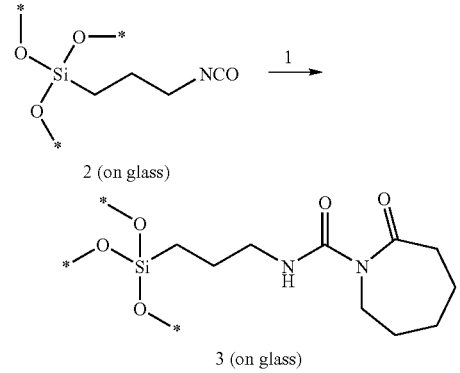

2 (on glass)

3 (on glass)

In this case, norbornene-substituted maleic anhydride 6 may be reacted with γ-aminopropyltriethoxysilane 7 to provide a substituted imide coupling activator compound 8. Coupling-initiator compound 8 can then undergo ring-opening metathesis polymerization (typically under catalytic conditions using rhodium, rhenium, or molybdenum alkylidene catalysts such as were developed by Grubbs or Schrock). Monomers such as cyclopentadiene, cyclooctadiene, dicyclopentadiene, norbornene or other monomers suitable for ROMP may be used to yield polymers such as illustrated by compound 9.

The coupling-initiator compounds may be bonded to an inorganic substrate. The inorganic substrate may comprise a plurality of glass fibers wherein at least one glass fiber is at least partially coated with the residue of a sizing composition comprising the coupling-initiator compound. As previously described, the silicon-coupling moiety S of the coupling-initiator compound that is included in the coated sizing composition may covalently bond to the glass fiber when the composition is coated and dried on the glass substrate, thereby securely attaching the coupling-initiator compound to the glass substrate.

Some embodiments of glass fibers may be used to reinforce polyamide resins. Polyamide resins reinforced with glass fibers in accordance with the invention may include Nylon 6, Nylon 6:6, Nylon 6:12, Nylon 4:6, Nylon 6:10, Nylon 12, polyamide 6T (polyhexamethylene terephthalamide), polyamide 6I (polyhexamethylene isophthalamide) or mixtures thereof among other polyamide resins. In one embodiment, the "I" moiety of the coupling-initiator compound in formula (II) above may include a blocked precursor of the active initiator moiety, e.g. a blocked isocyanate. In these embodiments, the precursor compound may be coated on the glass substrate and the active form of the initiator may be generated in situ on the surface of a glass substrate when exposed to unblocking conditions. This process may be illustrated by the reaction scheme D' below:

(D')

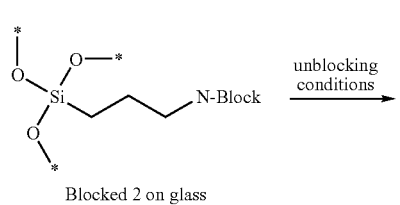

Blocked 2 on glass

The blocked isocyanate group may be obtained by reacting the isocyanate group of compound 2 in reaction scheme A' above with a compound that renders the isocyanate group unreactive. A suitable blocking agent for the isocyanate group may be determined by its ability to prevent the blocked isocyanate from reacting until a desired temperature is achieved.

Examples of compounds that may be suitable blocking agents include, but are not limited to, oximes such as methyl ethyl ketoxime, acetone oxime, and cyclohexanone oxime, lactams such as ε-caprolactam, and pyrazoles. Organosilicon compounds with a blocked isocyanate group are described in U.S. Patent Publication 2007/0123644, incorporated herein by reference for all purposes. Upon heating or other deblocking conditions, these blocked isocyanates decompose to free isocyanate and the blocking species. Deblocking temperatures depend on the blocking groups and typically are in the range from about 70° C. to about 200° C. The blocked isocyanate may be included as a component of the sizing composition used to size glass fibers, and may be applied to glass fibers in the manner previously described to form the entity identified as "blocked 2 on glass" in reaction scheme D' above.

When the glass fibers with blocked isocyanate compound are exposed to unblocking conditions, e.g. elevated temperatures during reactive extrusion of a glass-reinforced resin, the isocyanate group may become unblocked to form the active isocyanate compound 2 chemically bonded to the glass surface. Now unblocked, the isocyanate group is available to react with the caprolactam monomer 1 in reaction scheme A' above, thereby forming coupling-initiator compound 3 bonded to the glass surface. The coupling-initiator compound may then enter into the in situ polymerization reaction on the surface of the glass fibers. If the isocyanate is blocked with a monomer in the polymerization reaction; e.g. when the isocyanate is blocked by capolactam in the anionic ring-opening polymerization of caprolactam, the blocked isocyanate may not need to dissociate into the free isocyanate in order to facilitate the ring-opening polymerization reaction.

2b. Additional Exemplary Formula (II) Coupling-Initiator Compounds

Additional methods of making coupling-initiator compounds of Formula (II) may include direct sililation of a caprolactam-containing intermediate as shown in reaction scheme A" below:

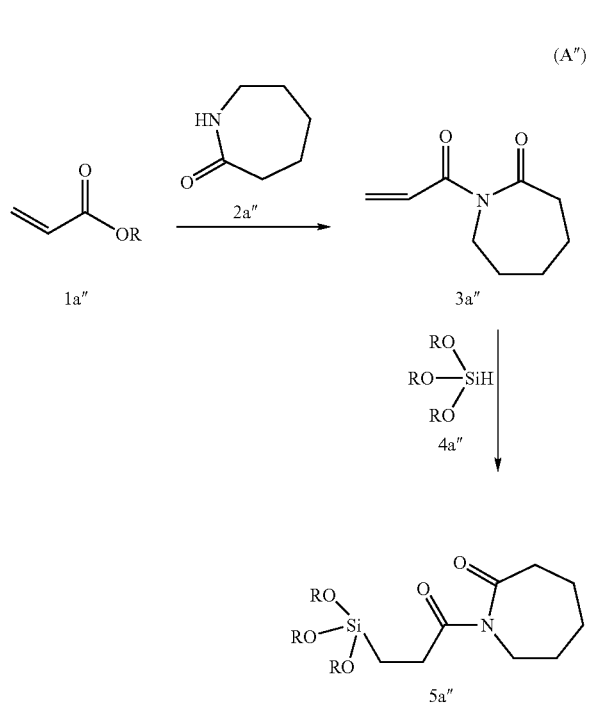

(A″)

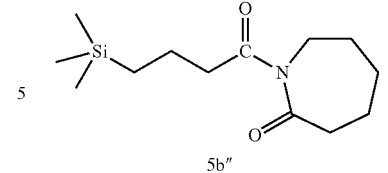

In reaction scheme A″, a methyl acrylate (1a″) is reacted with caprolactam (2a″) to produce the caprolactam-containing intermediate (3a″). The intermediate (3a″) was then directly sililated with alkoxysilane (4a″) to produce the final coupling-initiator compound (5a″). In the coupling-initiator reaction product (5a″), the silane-containing moiety is a trialkoxysilane group, the lining moiety is an ethylene (—CH₂—CH₂—) group, and the initiator moiety is the caprolactam group that can undergo a ring opening polymerization reaction under polymerization conditions.

Another exemplary reaction scheme B″ creates a caprolactam intermediate from an allyoyl chloride starting precursor, as shown below:

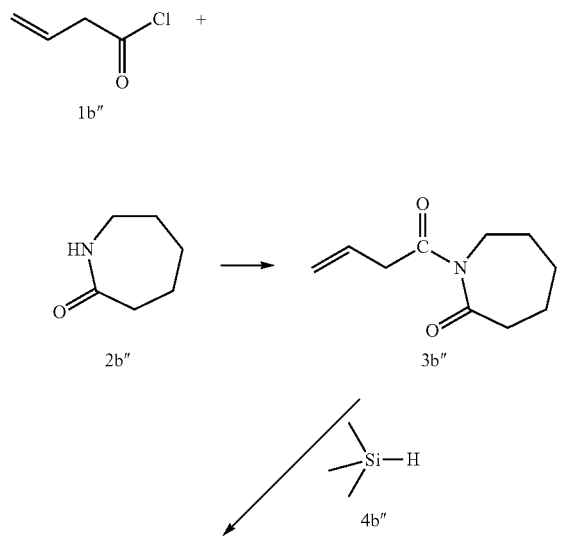

(B″)

In exemplary reaction scheme (B″), an allyoly chloride (1b″) is reacted with caprolactam (2b″) in a pyridine solution to produce the caprolactam-containing intermediate (3b″). The intermediate is then directly sililated with silane compound (4b″) to produce the coupling-initiator compound (5b″), with a propylene (—CH₂CH₂CH₂—) linking moiety.

3. Exemplary Formula (III) Coupling-Initiator Compounds

Examples of coupling-initiator compounds of Formula (III) include the products from a double Micheal adduct synthesis, such as the one described in exemplary reaction scheme E below:

Exemplary Reaction Scheme (E)

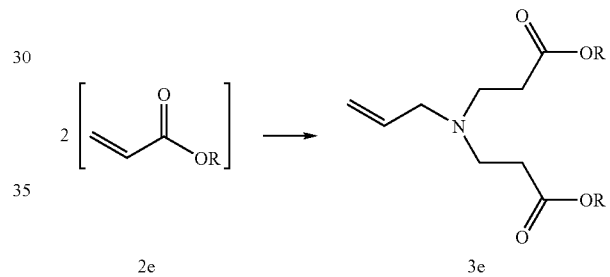

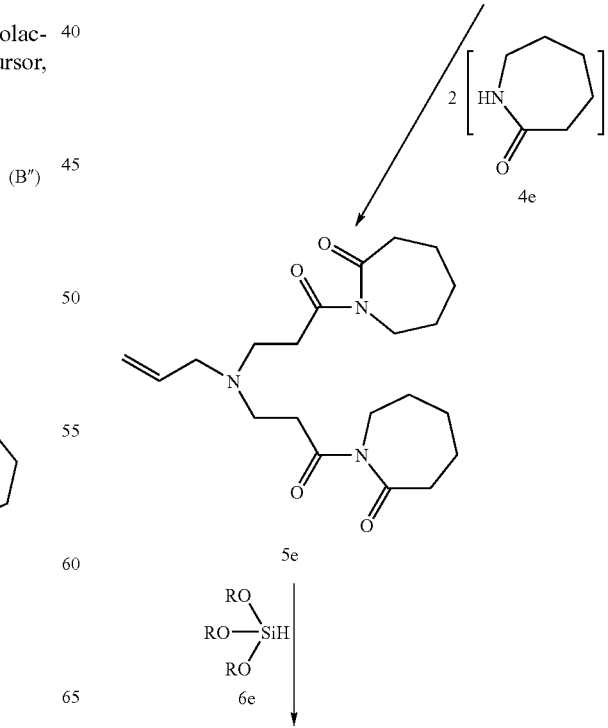

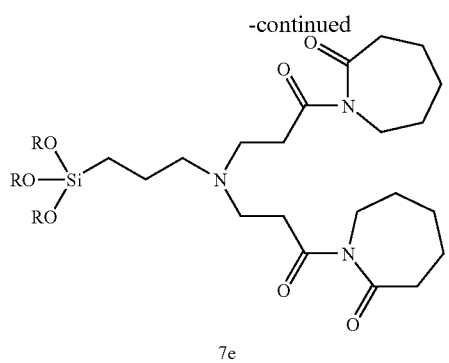

7e

In exemplary reaction scheme E, a coupling-initiator compound with two initiator sites is synthesized by starting with an unsaturated alkylamine (1e) and a methyl acrylate compound (2e) to produce a first intermediate compound (3e). The intermediate compound (3e) is reacted with caprolactam (4e) to produce a second intermediate compound (5e) that has two initiator moieties for ROMP. The second intermediate compound (5e) is reacted with a trialkoxy silane compound (6e) to form the silicon-containing coupling moiety on the final coupling-initiator compound (7e).

Alternatively, coupling-initiator compounds of Formula (III) may be made by first forming intermediates containing the initiator moieties (3f) from a methyl acrylate compound (1f) and a caprolactam (2f). The intermediates (3f) may then be reacted with a silicon-containing Micheal donor (4f) to produce the final coupling-initiator compound (5f). Exemplary reaction scheme F summarizes this process of making dual-initiator coupling-initiator compounds of Formula (III):

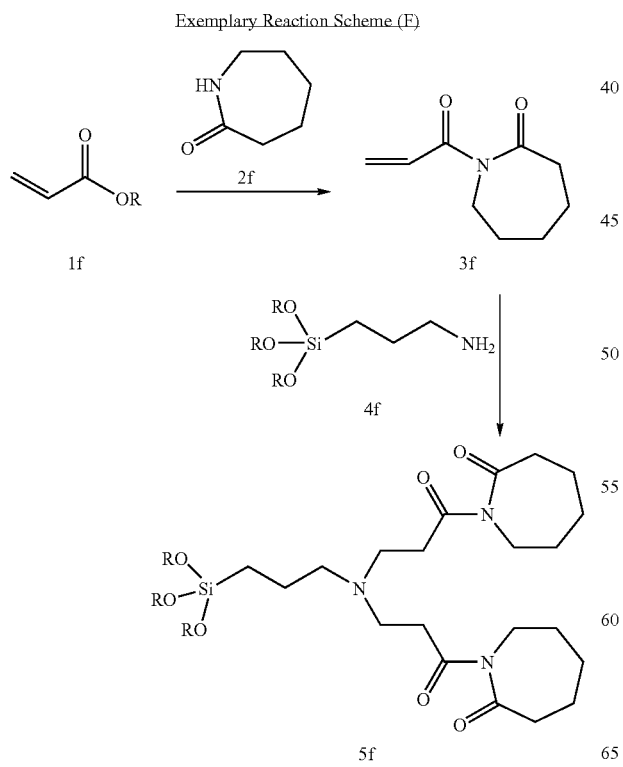

In exemplary reaction scheme F, the silicon-containing Michael donor (4f) is an amino silane. Michael donors may also include allyl amines and mercapto silanes, among others.

In another alternate synthesis pathway, coupling-initiator compounds of Formula (III) may be made by reacting a silicon-containing Michael donor (1g) with another reactant (2g) that includes at least two reactive sites for the addition of caprolactams (4g). The starting reactants react to form a first intermediate (3g) that includes the silicon-containing coupling moiety and at least two reactive sites for caprolactam (4g). The intermediate (3g) is reacted with the caprolactam (4g) to make the final coupling-initiator compound (5g) having two polymerization initiator moieties. Exemplary reaction scheme G below summarizes this alternate synthesis pathway with dimethyl maleate used as a starting reactant (2g):

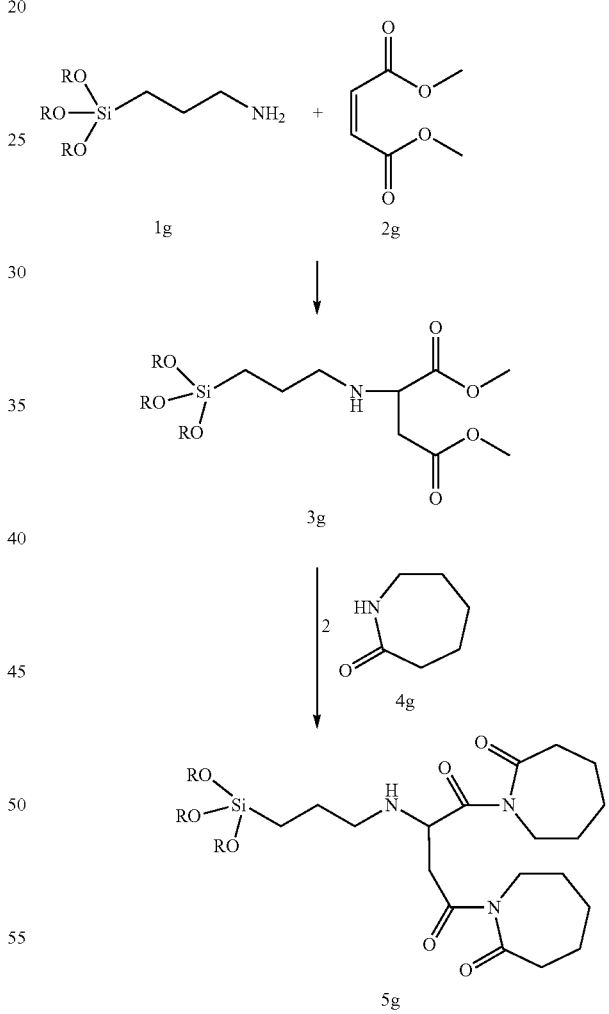

Sizing Compositions $ Fiber Composites That Include Coupling-Initiator Compounds Sizing compositions may be prepared by adding a coupling-initiator compounds to water and/or other suitable solvents to form a solution. The sizing composition may also include other sizing composition components, such as film-forming polymers, lubricants, defoamers, biocides, and silanes, among other components. The sizing composition should contain an amount of one or more coupling-initiator compounds sufficient to accomplish the desired participation in the ring-opening polymerization. The overall concentration of the coupling-initiator compounds and other components in the sizing composition can be adjusted over a wide range according to the means of application to be used, the character of the inorganic reinforcing material to be sized, and the intended use of the sized inorganic reinforcing material, among other considerations. In one embodiment, the sizing composition may contain about 5 wt % of the coupling-initiator compound. The components may be added sequentially, or they may be pre-diluted before they are combined to form the sizing composition.

The sizing composition may be applied to the inorganic substrate by a variety of methods. For example, the sizing composition may be applied to glass fibers pulled from a bushing using a kiss-roll applicator. Other ways of applying the sizing composition may include contacting glass fibers with other static or dynamic applicators, such as a belt applicator, spraying, and/or dipping, among other application methods. Alternatively, the coupling-initiator compound may be added to the binder used in the process of forming woven or non-woven mats.

After the sizing composition has been applied, fibers may be collected in rovings or may be chopped to form chopped strands. Rovings of continuous sized strands may be used in some applications, e.g. in long-fiber thermoplastics, or the rovings may be comingled and may be later chopped to a desired length. The length and diameter of the chopped glass fibers used for reinforcing polyamide resins may be determined by various factors such as, but not limited to, the ease of handling when glass fibers are melt-kneaded with a polyamide resin, the reinforcing effect of the glass fibers, glass fiber dispersing ability, the type of polyamide resin in which the chopped glass fiber will be used to reinforce and the intended use of a glass-reinforced polyamide resin article. In some embodiments, the length of the chopped glass fiber strand may range from about 1 mm to about 50 mm. For example, chopped glass fibers used to reinforce Nylon-6 may have a strand length of about 6 mm. After the fiber strands have been chopped, they may then be dried until the moisture level of the fibers is sufficiently low, e.g. below about 0.1%.

Examples of glass fibers that may be used include, without limitation, fibers prepared from fiberizable glass compositions such as "E-glass", "A-glass", "C-glass", "S-glass", "ECR-glass" (corrosion resistant glass), "T-glass", and fluorine and/or boron-free derivatives thereof. Exemplary formulations of glass fibers are disclosed in K. Lowenstein, The Manufacturing Technology of Continuous Glass Fibers (Third Ed. 1993), incorporated herein by reference for all purposes.

The coupling-initiator compounds may be used in reinforced resin materials. Processes of preparing these reinforced resin materials may include applying a sizing composition with one or more coupling-initiator compounds to a glass substrate. The sized glass substrate may be mixed with a lactam monomer and a polymerization catalyst to form a polymerization mixture, and the mixture may be exposed to conditions sufficient to cause an in situ anionic ring-opening polymerization of the lactam monomer, thereby forming a polymer/glass matrix in which the glass substrate is grafted to the polyamide polymer. The polymerization is referred to as "in situ" because the polymer is formed directly on the surface of the glass substrate, as opposed to being first formed and then coated on the glass surface. As a result, the coupling of the glass component and the polymer component of the composite material is substantially improved over conventional glass-reinforced resins.

Reinforced resin materials of the invention may be produced using processing procedures such as reactive extrusion, resin transfer molding, pultrusion, and reaction injection molding. Example 1 below illustrates the production of glass-reinforced polyamide-6 using the process of the invention in a reactive extrusion process, and for comparative purposes, Example 2 below illustrates the production of a glass-reinforced polyamide-6 using a conventional reactive extrusion process:

Example 1

Chopped fiber strands sized with a sizing composition comprising 2-oxo-N-(3-(triethoxysilyl)propyl)azepane-1-carboxamide (compound 3 in reaction scheme A' above) may be fed into an extruder as previously described. A monomer mix comprising caprolactam monomer 1 and sodium caprolactam catalyst 4, as shown in reaction scheme B' above, may also be fed into the extruder to be mixed and heated with the sized glass fibers. The processing conditions within the extruder initiate and complete an anionic ring-opening polymerization of the caprolactam 1 in accordance with reaction scheme B', and strands of the resulting glass-reinforced Nylon-6 may be extruded through the extruder die. A sample strand of the glass-reinforced Nylon-6 may be broken under tension. The breaking point may be analyzed with a Scanning Electron Microscope (SEM) to show the outstanding coupling of glass and polymer in the composite material provided by the present invention.

Example 2

Chopped glass fibers strands may be sized with a conventional sizing composition comprising 0-30 wt % of γ-aminopropyltriethoxysilane or other suitable silane coupling agent, 20-70 wt % of a polyurethane emulsion or a suitable mixture of emulsions, and 10-50 wt % of a lubricant or mixture of lubricants, and 0-50 wt % of any other required or preferred additives. The chopped sized fibers may be fed into the same extruder used in Example 1 above. Referring to reaction scheme H below, monomer mix comprising caprolactam monomer 1, sodium caprolactam catalyst 4 and a commercially-available activator 5 may also be fed into the extruder, thereby mixing and heating the mix with the sized glass fibers. The processing conditions within the extruder initiate and complete an anionic ring-opening polymerization of the caprolactam monomer 1 within the extruder in accordance with reaction scheme H below:

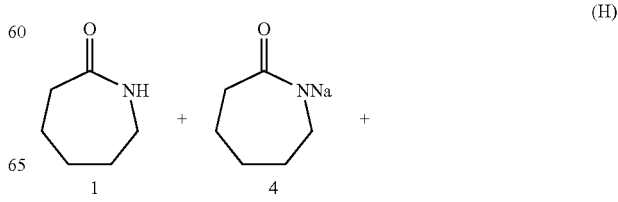

(H)

-continued

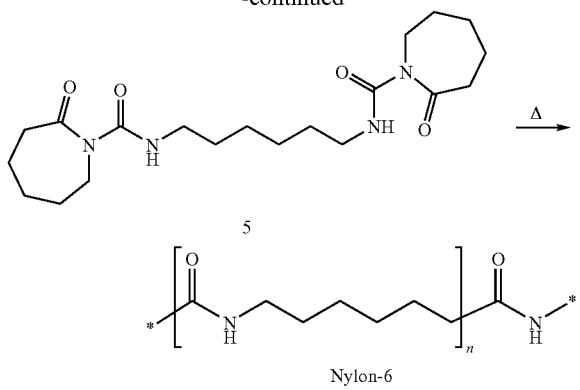

Strands of the resulting Nylon-6 may then be obtained from the extruder die and analysis of the breaking point of a broken strand may be performed to show only average coupling between the glass and the polymer matrix. The comparison between the products of Examples 1 and 2 clearly demonstrate the unexpected and superior results achieved by the present invention.

In another embodiment, substrates may be used in a resin transfer molding process. For example, glass fibers may be dispersed in a closed mold and a mixture comprising lactam monomer and polymerization catalyst may be transferred into the mold to form a polymerization mixture. The mold walls may be heated to a temperature sufficient to cause ring-opening polymerization of the monomer and result in the formation of the glass-reinforced resin material in the mold shape. The mold may then be opened to provide a shaped glass-reinforced resin article.

In another embodiment, the described coupling-initiator compounds and methods may be used to simplify the preparation of woven and non-woven fabric laminates using vacuum-assisted resin transfer molding. These materials may be used to make high-end composites for applications such as wind turbine blades, automotive or aircraft parts, and reinforced pressure vessels. Current processes typically utilize a two-component application wherein a first molten mixture comprising lactam monomer and polymerization catalyst and a second molten mixture comprising lactam monomer and activator compound are separately mixed with glass fibers containing conventional sizing. In a vacuum-assisted resin transfer molding process, one mixture that contains a lactam monomer and polymerization catalyst may be used to cover glass fibers containing the present coupling-initiator compounds.

In another embodiment, processes may include using sized substrates in a pultrusion process. For example, glass fibers containing one or more of the present coupling-initiator compounds may be pulled from a creel through a bath comprising a composition of lactam monomer and polymerization catalyst to impregnate the fibers. The impregnated glass fibers may then enter a heated die that has been machined to the final shape of the article to be produced. While the impregnated glass fibers are being pulled through the die, the heat causes polymerization of the lactam monomer and the formation of the glass-reinforced resin, which exits the die in the desired shape. The shaped resin may then be cut to the desired length.

In still other embodiments, processes may include the use of substrates containing the present coupling-initiator compounds in a reaction injection molding process. For example, glass fibers sized with one or more coupling-initiator compounds may be dispersed in a liquid composition comprising lactam monomer and polymerization catalyst. The liquid composition may then be injected into a mold and heated to cause anionic ring-opening polymerization of the lactam monomer. After polymerization is completed, the shaped glass-reinforced resin may be removed from the mold.

One skilled in the art can easily ascertain the essential characteristics of this invention from the foregoing description, and without departing from the spirit and scope thereof, can make various changes and modifications of the invention to adapt it to various usages and conditions.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the coupling-initiator compound" includes reference to one or more coupling-initiator compounds and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:
1. A coupling-initiator compound having the formula:

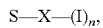

wherein n is an integer having a value between 2 and 5;
S comprises a silicon-containing coupling moiety through which the coupling-initiator compound bonds to a substrate surface;
X comprises a linking moiety to link the S moiety with the one or more I moieties; and
(I)$_n$ comprises one or more polymerization initiator moieties, wherein each of the initiator moieties is capable of initiating a polymerization of a monomer under polymerization conditions, and wherein each of the initiator moieties may be the same or different.

2. The coupling-initiator compound of claim 1, wherein the silicon-containing coupling moiety (S) comprises:

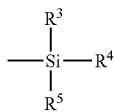

wherein $R^3$, $R^4$ and $R^5$ are the same or different, and are selected from the group consisting of an alkyl group, an aryl group, an alkoxy group, a halogen group, and an alkylcyclic group.

3. The coupling-initiator compound of claim 2, wherein $R^3$, $R^4$ and $R^5$ each independently comprise a $C_1$ to $C_5$ alkoxy group.

4. The coupling-initiator compound of claim 1, wherein the linking moiety (X) is selected from the group consisting of carbon (—C—), nitrogen (—N—), oxygen (—O—), sulphur (—S—), silicon (—Si—), an amine group, an amide group, an aromatic group, a urethane group, a urea group, an ether group, and an ester group.

5. The coupling-initiator compound of claim 1, wherein at least one of the initiator moieties (I) comprises a $C_1$ to $C_9$, substituted or unsubstituted, organo-cyclic ring.

6. The coupling-initiator compound of claim 1, wherein the organo-cyclic ring comprises at least one heteroatom selected from the group consisting of nitrogen, oxygen, silicon, and sulphur.

7. The coupling-initiator compound of claim 1, wherein the organo-cyclic ring comprises:

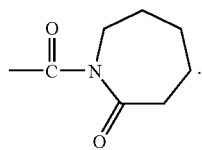

8. The coupling-initiator compound of claim 1, wherein the one or more initiator moieties initiate an in situ ring-opening polymerization reaction with the monomer in the presence of a polymerization catalyst.

9. The coupling-initiator compound of claim 1, wherein the substrate surface comprises a fiberglass surface.

* * * * *